United States Patent
Ezaki et al.

(10) Patent No.: US 9,733,205 B2
(45) Date of Patent: Aug. 15, 2017

(54) SENSOR AND SENSOR SYSTEM EQUIPPED WITH SAME

(75) Inventors: Hirofumi Ezaki, Ehime (JP); Akihisa Higashihara, Ehime (JP)

(73) Assignee: Panasonic Healthcare Holdings Co., Ltd., Tokyo (JP)

( * ) Notice: Subject to any disclaimer, the term of this patent is extended or adjusted under 35 U.S.C. 154(b) by 509 days.

(21) Appl. No.: 14/123,099

(22) PCT Filed: Jun. 11, 2012

(86) PCT No.: PCT/JP2012/003787
§ 371 (c)(1),
(2), (4) Date: Nov. 28, 2013

(87) PCT Pub. No.: WO2012/172772
PCT Pub. Date: Dec. 20, 2012

(65) Prior Publication Data
US 2014/0102895 A1    Apr. 17, 2014

(30) Foreign Application Priority Data
Jun. 16, 2011    (JP) .................................. 2011-134144

(51) Int. Cl.
*G01N 27/327* (2006.01)

(52) U.S. Cl.
CPC ..... *G01N 27/3277* (2013.01); *G01N 27/3272* (2013.01)

(58) Field of Classification Search
CPC .............................. G01N 27/327; C12Q 1/001
USPC ............. 204/403.01–403.15; 205/777.5, 792
See application file for complete search history.

(56) References Cited

U.S. PATENT DOCUMENTS

| | | | |
|---|---|---|---|
| 5,628,890 A | * | 5/1997 | Carter .................... C12Q 1/001 204/403.05 |
| 6,939,450 B2 | | 9/2005 | Karinka et al. |
| 7,122,110 B2 | | 10/2006 | Deng et al. |
| 8,430,999 B2 | | 4/2013 | Onoda et al. |
| 2002/0175075 A1 | | 11/2002 | Deng et al. |
| 2004/0067166 A1 | | 4/2004 | Karinka et al. |

(Continued)

FOREIGN PATENT DOCUMENTS

| | | |
|---|---|---|
| JP | 2002-526759 A | 8/2002 |
| JP | 2003-004691 A | 1/2003 |

(Continued)

OTHER PUBLICATIONS

Office Action from the corresponding Japanese Patent Application No. 2013-520429 issued on Feb. 16, 2016.

(Continued)

*Primary Examiner* — Bach Dinh
(74) *Attorney, Agent, or Firm* — Shinjyu Global IP

(57) ABSTRACT

This sensor has a diverter, such as a convex portion (608) and a concave portion (508), on the side wall (408) of a cavity (308). A biological sample deposited in a suction opening (52) is drawn into the cavity (308) by capillary action, but if the amount of biological sample is too small, either the biological sample is prevented from moving forward by the convex portion (608) and the concave portion (508), or the time it takes to reach a detecting electrode (33) is increased, which provides the user enough time to supply additional biological sample before a false detection occurs.

2 Claims, 18 Drawing Sheets

(56) References Cited

U.S. PATENT DOCUMENTS

| | | | |
|---|---|---|---|
| 2004/0134779 | A1 | 7/2004 | Hsu et al. |
| 2004/0216516 | A1* | 11/2004 | Sato .................. B01L 3/502715 |
| | | | 73/64.56 |
| 2006/0037870 | A1 | 2/2006 | Deng et al. |
| 2006/0228254 | A1 | 10/2006 | Kusaka et al. |
| 2007/0131565 | A1* | 6/2007 | Fujiwara ................ C12Q 1/001 |
| | | | 205/777.5 |
| 2009/0071847 | A1* | 3/2009 | Edelbrock ............ G01N 27/327 |
| | | | 205/778 |
| 2009/0120806 | A1 | 5/2009 | Onoda et al. |
| 2009/0321257 | A1 | 12/2009 | Takahara et al. |
| 2010/0270177 | A1 | 10/2010 | Fujiwara et al. |
| 2011/0079522 | A1 | 4/2011 | Webster et al. |
| 2014/0158553 | A1 | 6/2014 | Fujiwara et al. |
| 2016/0077040 | A1 | 3/2016 | Fujiwara et al. |

FOREIGN PATENT DOCUMENTS

| | | | |
|---|---|---|---|
| JP | 2004-279150 | A | 10/2004 |
| JP | 2006-509187 | A | 3/2006 |
| JP | 2007-521498 | A | 8/2007 |
| JP | 2010-032501 | A | 2/2010 |
| JP | 2010-243514 | A | 10/2010 |
| JP | 4611208 | B2 | 10/2010 |
| JP | 2011-080990 | A | 4/2011 |
| WO | 00/20626 | A1 | 4/2000 |
| WO | 2005/078436 | A1 | 8/2005 |
| WO | 2007/026683 | A1 | 3/2007 |

OTHER PUBLICATIONS

Office Action from the corresponding Japanese Patent Application No. 2013-520429 issued on Jul. 21, 2015.
E-mail "[06846] Protecting Hydrology Science from Reinvention by corrupt Lay People colluding with USPTO—US Pat Application 20140102895" dated Apr. 18, 2014.
Fuji Electric—Ongoing Massive Patent Violations URL: http://terror-tubarc.blogspot.com.br/2014/04/fuji-electric-ongoing-massive-patent.html.
USP, Harvard, MIT, PSU, Duke, and USPTO are Raping Hydrology I URL: http://terror-tubarc.blogspot.com.br/2014/01/usp-harvard-mit-psu-duke-and-uspto-are.html.
UC Santa Barbara—Dishonoring Hydrology I, II, III URL: http://terror-tubarc.blogspot.com/2013/12/uc-santa-barbara-dishonoring-hydrology-i.html; http://terror-tubarc.blogspot.com.br/2013/12/uc-santa-barbara- dishonoring-hydrology.html; http://terror-tubarc.blogspot.com.br/2013/12/uc-santa-barbara-dishonoring-hydrology_24.html, dated Dec. 25, 2013.
Medtronic, Inc. is Screwing Up Hydrology Science URL: http://terror-tubarc.blogspot.com.br/2013/11/medtronic-inc-is-screwing-up-hydrology.html, dated Nov. 2, 2013.
CareFusion Corporation—USPTO is Cheating on Science URL: http://terror-tubarc.blogspot.com.br/2013/10/carefusion-corporation-uspto-is.html, dated Oct. 11, 2013.
Carnegie—Understanding Terror inside US Government I, II, III, IV, and V URL: http://terror-tubarc.blogspot.com.br/2013/08/carnegie-understanding-terror-inside-us_7959.html; http://terror-tubarc.blogspot.com.br/2013/08/carnegie-understanding-terror-inside-us_19.html; http://terror-tubarc.blogspot.com.br/2013/08/carnegie-understanding-terror-inside-us_8512.html; http://terror-tubarc.blogspot.com.br/2013/08/carnegie-understanding-terror-inside-us_6606.html; http://terror-tubarc.blogspot.com.br/2013/08/carnegie-understanding-terror-inside-us_7959.html, dated Aug. 20, 2013.
Johnson Controls Inc.—Understanding Terror inside US Government, Inside Terrorists—Broad Assault on a 'Scientific Breakthrough', JCI manufactures batteries ignoring Advanced Hydrology—Now Boeing feels the pain when batteries leak and burn! URL: http://terror-tubarc.blogspot.com.br/2013/08/johnson-controls-inc-understanding_2922.html, dated Aug. 3, 2013.
CareFusion Corporation—Assaulting a 'Scientific Breakthrough', Inside Terrorists—Shamefully Assaulting a 'Scientific Breakthrough' URL: http://terror-tubarc.blogspot.com.br/2013/06/carefusion-corporation-assaulting.html, dated Jun. 27, 2013.
Roche—Understanding Terror inside US Government I and II URL: http://terror-tubarc.blogspot.com.br/2013/04/roche-understanding-terror-inside-us.html; http://terror-tubarc.blogspot.com.br/2013/04/roche-understanding-terror-inside-us_18.html, dated Apr. 18, 2013.
Medtronic, Inc. is Ignoring Hydrology Science, What kind of reliable company would do such a mess ignoring the Law, Ethics, IP rights, and science? URL: http://illumina-tubarc.blogspot.com.br/, dated Nov. 29, 2013.
Pledging SUNY to Respect Hydrology URL: http://suny-tubarc.blogspot.com.br/, dated Nov. 8, 2012.
Protecting Hydrology Science from Reinvention URL: http://hydrotechnology.blogspot.com.br/, dated Oct. 10, 2011.
International Search Report of PCT Application No. PCT/JP2012/003787.
Notice of Allowance from the corresponding Japanese Patent Application No. 2013-520429 issued on Jun. 7, 2016.

* cited by examiner

SENSOR AND SENSOR SYSTEM EQUIPPED WITH SAME

CROSS-REFERENCE TO RELATED APPLICATIONS

This application is a national stage filing under 35 U.S.C. §371, and claims benefit of priority to PCT Application Number PCT/JP2012/003787 filed on Jun. 11, 2012, which claims priority to Japanese Patent Application No. 2011-134144 filed on Jun. 16, 2011. The entire disclosures of PCT Application Number PCT/JP2012/003787 and Japanese Patent Application No. 2011-134144 are hereby incorporated herein by reference.

TECHNICAL FIELD

The present invention relates to a sensor used in the detection and/or quantification of a target substance (such as blood glucose) contained in a biological sample, and to a sensor system equipped with this sensor.

BACKGROUND

Biological sample measurement devices that measure biological data such as blood glucose level have been used in the past. A sensor is mounted to a measurement device such as this (hereinafter referred to simply as "sensor"). The sensor is provided with a cavity and suction opening. When a biological sample is deposited in the suction opening, the biological sample is guided into the cavity by capillary action. A specific voltage is applied to the sensor electrode in the measurement device, and the output value from the output electrode is measured, thereby acquiring information about the blood glucose level, etc.

With a sensor such as this, accurate measurement cannot be performed unless the sample reaches the electrode disposed inside the sensor.

In view of this, Japanese Laid-Open Patent Application 2003-004691 discloses an electrochemical sensor that outputs an error signal if there is an insufficient sample containing the substance to be analyzed, and that prompts the user to redo the measurement.

SUMMARY

When taking user convenience into account, it is preferable if the user can carry out measurement just by adding more of the biological sample, rather than ending the measurement, particularly if at first the user did not supply enough of the biological sample.

However, if the length of time from when the sensor is mounted to the measurement device until an error message is displayed is extended in order to provide enough time to add more biological sample, there will be situations in which the system concludes that there is enough biological sample for measurement despite the fact that the amount of biological sample is actually insufficient for measurement.

This can happen for a number of reasons. One reason is due to wicking, in which the biological sample moves along the inner walls of the cavity and reaches the detecting electrode inside the sensor. Another reason is if the biological sample seeps through to the reagent layer, so that the biological sample reaches the detecting electrode even though there is an insufficient amount of biological sample for measurement.

It is an object of the present invention to provide a sensor that prevents false detection caused by wicking, while allowing measurement to continue by adding more biological sample even if an insufficient amount of biological sample was added at first, and to provide a measurement device equipped with this sensor.

The sensor pertaining a first embodiment is a sensor that is used in the detection and/or quantification of a target substance contained in a biological sample, said sensor comprising:
  a cavity;
  a suction opening that goes from the outside of the sensor to the inside of the cavity;
  an electrode provided inside the cavity; and
  a diverter having at least one of a concave portion and a convex portion, the at least one of a concave portion and a convex portion being provided to the inner wall of the cavity.

With this sensor, a biological sample deposited in the suction opening is drawn into the cavity by capillary action, but if there is too little biological sample, either the biological sample is prevented from moving forward by a convex portion and/or a concave portion, or the time it takes to reach a detecting electrode after the biological sample has been deposited is increased.

Consequently, the diverter makes the path from the suction opening to the electrode longer, so false detection of the biological sample caused by wicking can be prevented. Furthermore, this provides the user enough time to supply additional biological sample before a false detection occurs.

The sensor pertaining to a second embodiment is a sensor that is used in the detection and/or quantification of a target substance contained in a biological sample, said sensor comprising:
  a cavity having a first end and a second end;
  a suction opening that is provided at the first end of the cavity and goes to the outside of the sensor; and
  an electrode that is disposed closer to the second end than to the first end inside the cavity,
  wherein, if we let D1 be the distance from the first end to the second end along the side wall of the cavity, and D2 be the linear distance from the first end to the second end, the relationship $D1 \geq 1.05 \times D2$ is satisfied, and preferably the relationship $D1 \geq 1.65 \times D2$ is satisfied.

With this sensor, since the diverter makes the path from the suction opening to the electrode longer, it takes any biological sample that has moved along the inner wall longer to reach the electrode.

The longer path prevents false detection, of the amount of biological sample, caused by wicking. Furthermore, this provides the user enough time to supply additional sample before a false detection occurs.

With the present invention, if too little biological sample is deposited, either the biological sample is prevented from moving forward, or the time it takes for a false detection to occur after the biological sample has been deposited is extended. This provides the user enough time to supply more of the biological sample before a false detection occurs.

DETAILED DESCRIPTION

Selected embodiments will now be explained with reference to the drawings. It will be apparent to those skilled in the art from this disclosure that the following descriptions of the embodiments are provided for illustration only and not for the purpose of limiting the invention as defined by the appended claims and their equivalents.

1. Sensor (1-1) A Simplified Configuration of the Sensor

A sensor 1 is an example of a sensor that is used in the detection and/or quantification of a target substance contained in a biological sample.

Figure 1:
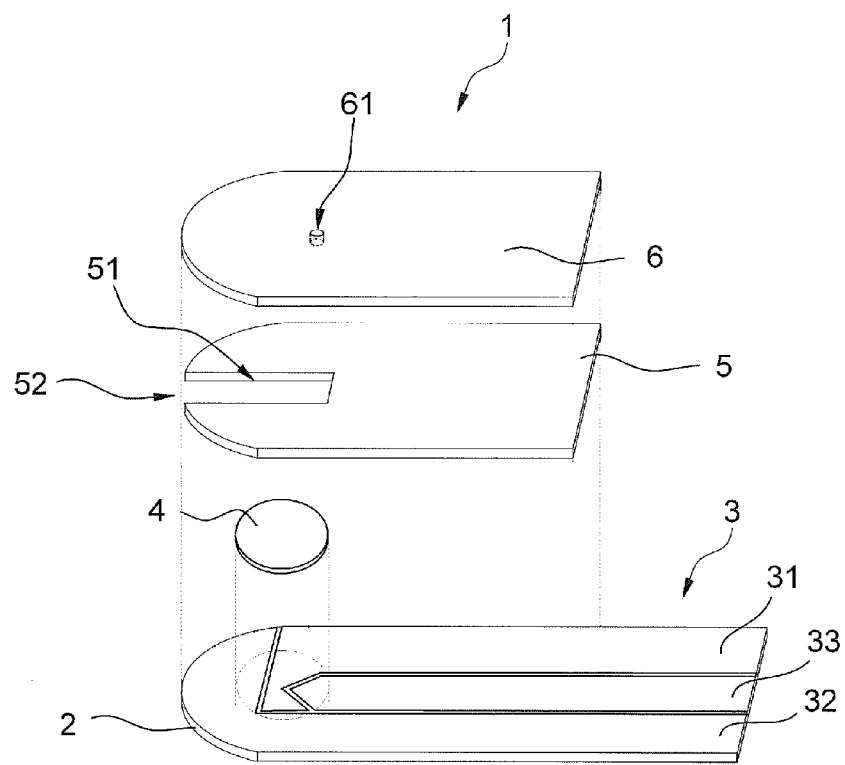
FIG. 1 is an exploded oblique view of a simplified configuration of a sensor.
Figure 2:
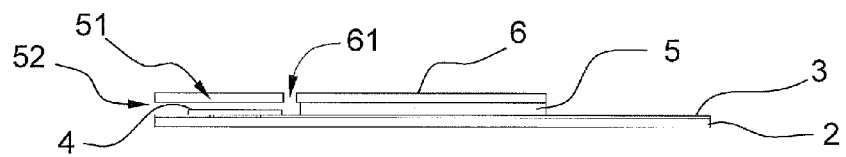
FIG. 2 is a cross section of a simplified configuration of a sensor.
Figure 3:
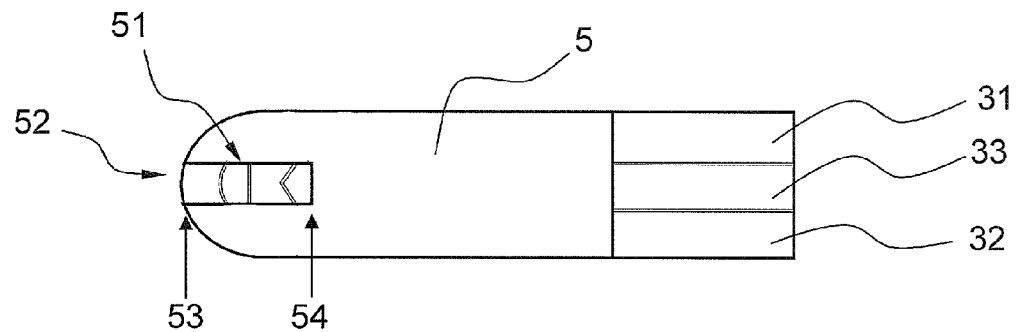
FIG. 3 is a plan view of a simplified configuration of a sensor, in which a cover is not shown.

As shown in FIGS. 1 to 3, the sensor 1 comprises a substrate 2, a conductor layer 3, a reagent layer 4, a spacer 5, and a cover 6.

(1-2) Substrate

As shown in FIGS. 1 and 2, the substrate 2 is a flat member. The substrate 2 has insulating properties. Examples of materials that can comprise the substrate 2 include polyethylene terephthalate, vinyl polymers, polyimide, polyester, styrenics, and other such resins; glass; and ceramics.

There are no particular restrictions on the dimensions of the substrate 2, but the width of the substrate 2, for example, is preferably 3 to 20 mm, and more preferably 5 to 10 mm. The length of the substrate 2 is preferably 10 to 40 mm. The thickness of the substrate 2 is preferably 0.05 to 2 mm, and more preferably 0.1 to 1 mm. The width, length, and thickness of the substrate 2 are preferably all within the above ranges.

(1-3) Conductor Layer

As shown in FIGS. 1 and 2, the conductor layer 3 is formed on the substrate 2, and has a substantially uniform thickness. The conductor layer 3 includes three electrodes 31 to 33. As shown in FIG. 1, a portion of each of the electrodes 31 to 33 is disposed so as to face a cavity 51.

As shown in FIG. 3, the electrode 32, the electrode 31, and the electrode 33 are disposed in that order inside the cavity 51, from a first end 53 to a second end 54 of the cavity 51. The electrode 31 is sometimes called a working electrode, the electrode 32 a counter electrode, and the electrode 33 a detecting electrode.

As will be discussed below, when the biological sample reaches the working electrode 31 and the detecting electrode 33, there is a change in the current value between the working electrode 31 and the detecting electrode 33. A measurement device 101 (discussed below) detects from this change that a biological sample has been deposited, and starts measurement. The measurement device 101 can also use a change in the current value between the working electrode 31 and the counter electrode 32 to measure the concentration of a target substance in the biological sample.

Each electrode may be formed by printing or the like in which a conductive material is used, or by covering the substrate 2 with a conductive material and then forming a non-conductive track by laser ablation or the like. For example, the conductor layer 3 can be formed by sputtering palladium onto the substrate 2, and forming a non-conductive track by laser ablation. The non-conductive track preferably has a width of 0.01 to 0.5 mm, and more preferably 0.05 to 0.3 mm.

There are no particular restrictions on the material of the conductor layer 3, so long as it is a conductive material (conductive substance). Examples of conductive materials include inorganic conductive substances, typified by metals, metal mixtures, alloys, metal oxides, and metal compounds; organic conductive substances, such as hydrocarbon-based conductive polymers and hetero atom-containing conductive polymers; and combinations of these. The material used for the conductor layer 3 is preferably palladium, gold, platinum, carbon, or the like.

The thickness of the conductor layer 3 can be varied according to how the layer is formed and the material of which it is made. For example, if the conductor layer 3 is formed by sputtering, the thickness of the conductor layer 3 is preferably 0.1 to 20 nm, and more preferably 1 to 10 nm. If the conductor layer 3 is formed by printing, the thickness of the conductor layer 3 is preferably 0.1 to 50 μm, and more preferably 1 to 30 μm.

(1-4) Reagent Layer

As shown in FIGS. 1 and 2, the reagent layer 4 is disposed touching the electrodes 31 to 33.

The reagent layer 4 functions as the active component of the sensor 1 along with the electrodes 31 and 32. The "active component" is the region that is electrochemically active, and is the portion that reacts with a specific substances in the biological sample, producing an electrical signal. More specifically, the reagent layer 4 includes an enzyme and an electron acceptor.

The reagent layer 4 may be disposed so as to be in contact with part of at least the electrodes 31 and 32 (the first electrode and the second electrode). The reagent layer 4 may further be disposed so as to be in contact with the electrode 33.

The reagent layer 4 has an electron acceptor and an enzyme.

The amount of electron acceptor contained in the reagent layer 4 can be set to an amount that is enough for the sensor to function, and is preferably set to between 1 and 500 nmol, and more preferably about 10 to 200 nmol, per measurement or per sensor 1.

The amount in which the enzyme is contained in the reagent layer 4 is set to be enough to detect the target substance, and is preferably set to between 0.2 and 20 U (units), and more preferably about 0.5 to 10 U, per sensor 1 or per measurement.

A redox enzyme can be used favorably as the enzyme. A "redox enzyme" encompasses oxidative enzymes and dehydrogenation enzymes. Examples of redox enzymes include the following. Glucose oxidase and glucose dehydrogenase are preferable as enzymes in which glucose is the substrate; lactic acid oxidase and lactic acid dehydrogenase are preferable as enzymes in which lactic acid is the substrate; cholesterol esterase and cholesterol oxidase are preferable as enzymes in which cholesterol is the substrate; alcohol oxidase is preferable as an enzyme in which alcohol is the substrate; and bilirubin oxidase is preferable as an enzyme in which bilirubin is the substrate.

The reagent composition may include a co-enzyme that matches the enzyme.

The role of the electron acceptor when the reagent layer 4 includes an enzyme that oxidizes the substrate will be described. The enzyme oxidizes the substrate and thereby takes electrons from the substrate and gives electrons to the co-enzyme. As a result, the co-enzyme goes from an oxidant to a reductant.

An electron acceptor, which is an oxidant, takes electrons from a co-enzyme that has become a reductant, and returns the co-enzyme to being an oxidant. As a result, the electron acceptor itself becomes a reductant. The electron acceptor that has become a reductant gives electrons to the electrode 31 or 32, and itself becomes an oxidant. In this way, the electron acceptor mediates electron movement between the enzyme and the electrodes.

The above-mentioned co-enzyme may bond to an enzyme protein (enzyme molecule) and thereby be supported on the enzyme protein. The co-enzyme may also exist in a state of being separated from the enzyme protein.

The reagent layer 4 can be formed by various methods. Examples of formation methods include printing and coating.

The shape of the reagent layer 4 can be changed in many ways, including rectangular and circular shapes. The surface area of the reagent layer 4 (the surface area in the planar direction of the substrate 2) is determined according to the characteristics and size of the device. This surface area is preferably 1 to 25 mm², and more preferably 2 to 10 mm².

The amounts in which the enzyme, the electron acceptor, and other components are contained in the aqueous solution that used for coating are selected according to the required characteristics and size of the device.

(1-5) Spacer 5 and Cavity 51

As shown in FIGS. 1 and 2, the spacer 5 is a member that provides a space between the cover 6 and the conductor layer 3 formed on the substrate 2.

More specifically, the spacer 5 is a flat member that covers the entire conductor layer 3 except for the lead portions of the electrodes 31 to 33 and the cavity 51 portion. The spacer 5 comprises a cutout that exposes the end on the opposite side from the lead portion of the electrodes 31 to 33. This cutout is rectangular in FIGS. 1 and 3.

Because the spacer 5 has this cutout, the cavity 51 is surrounded by the spacer 5, the conductor layer 3, and the cover 6. Thus, the spacer 5 provides the side walls of the cavity 51, and can also specify the length, width, height, etc., of the cavity 51.

The volume of the cavity 51 is set to about 0.05 to 5.0 µL (microliters), and preferably about 0.1 to 1.0 µL. The thickness of the spacer 5 is about 0.02 to 0.5 mm, and preferably about 0.1 to 0.2 mm. The length of the cutout in the spacer 5 is preferably 1 to 5 mm. The width of the spacer 5 is about 0.25 to 4 mm, and preferably about 0.5 to 2 mm.

These dimensions should be suitably selected so that the cavity 51 will have the desired volume. For instance, if the spacer 5 has a thickness of 0.145 mm and comprises a cutout with a length of 3.4 mm and a width of 1.2 mm, the cavity 51 will have a length of 3.4 mm, a width of 1.2 mm, a height of 0.145, and a volume of approximately 0.6 µL.

The cavity 51 has a shape that is longer in the lengthwise direction of the sensor 1. The two ends in the lengthwise direction of the sensor 1 are called the first end 53 and the second end 54. A suction opening 52 is an opening provided at the first end 53, and leads from the outside of the sensor 1 to the inside of the cavity 51. The biological sample is drawn in by capillary action from the suction opening 52, and held on the electrodes 31 to 33. The shape of the cavity 51 will be discussed in detail below.

(1-6) Cover

As shown in FIGS. 1 and 2, the cover 6 is a flat member that covers the entire spacer 5.

The cover 6 comprises a hole that goes through from the front to the back. This hole functions as a vent opening 61 that leads from the cavity 51 to the outside. The vent opening 61 is an exhaust hole for letting air inside the cavity 51 escape from the cavity when a biological sample is drawn into the cavity 51.

Thus discharging the air makes it easier for the biological sample to be drawn into the cavity 51. The vent opening 61 is preferably provided at a location away from the suction opening 52, that is, deeper inside the cavity 51 as viewed from the suction opening 52. When the suction opening 52 is disposed in this way, the biological sample can quickly move from the suction opening 52 to the back of the cavity 51.

It is also preferable for the vent opening 61 to be disposed more to the back than the reagent layer 4 that is placed on the conductor layer of the sensor 1, and more to the front than the second end 54.

2. Shape of Cavity

The cavity 51 has a diverter. The diverter has a concave portion or a convex portion provided to the inner wall of the cavity 51.

The "inner wall" here encompasses a side wall provided between the first end 53 and the second end 54; a back wall provided at the end of the cavity 51, that is, to the second end 54; a bottom; and a ceiling that is opposite the bottom.

The side wall and back wall are formed in the thickness shape of the spacer 5, the bottom is formed by the upper face of the substrate 2, and the ceiling is formed by the lower face of the cover 6. That is, either the cutout of the spacer 5 has a concave portion or convex portion in the planar direction of the spacer 5, or a concave portion or convex portion is provided to the upper face of the substrate 2, or a concave portion or convex portion is provided to the lower face of the cover 6.

A biological sample deposited in the suction opening 52 is drawn into the cavity 51 by capillary action. The biological sample advances particularly well at the corner portions of the interior of the cavity 51, that is, at the portions where the spacer 5 and the cover 6 are joined, and the portions where the spacer 5 and the substrate 2 are joined.

When the biological sample works its way forward (wicking) along the edges of the side walls toward the back, and reaches the detecting electrode 33 disposed at the back of the cavity 51, there is the risk of a false detection that a biological sample has been introduced even though the amount of biological sample is inadequate.

To deal with this, with the sensor in this embodiment, a diverter is provided, which either prevents the biological sample from moving forward, or increases how long it takes to reach the detecting electrode 33. As a result, either false detection caused by wicking is suppressed, or the time it takes for a false detection to occur after the biological sample is deposited is extended. More specifically, the time until a false detection occurs should be about 30 seconds. This allows the user to deposit additional biological sample.

The shape of the diverter may be linear or it may be a curved shape, and is not limited to any specific shape.

The amount by which the concave portion and convex portion are recessed and protrude from the inner wall of the cavity 51 at the diverter may vary with the linear distance from the suction opening 52 to the detecting electrode 33. The amounts of recess and protrusion are preferably at least approximately 10% of the width of the cavity 51, and more preferably at least 17%. That is, if the cavity 51 is 1.2 mm wide, then the amounts of recess and protrusion should be about 120 to 500 mm.

Examples of various cavity shapes that can be applied to the sensor 1 will now be given. The electrodes other than the detecting electrode 33 will not be depicted in the drawings for the following description. Also, those members and portions having the same function are numbered the same, and will not be described again.

Also, in FIGS. 6 to 16, the shape of the side walls is in right and left symmetry, but the present invention is not limited to this, and the left and right side walls may have different shapes.

(1) First Mode

Figure 4:
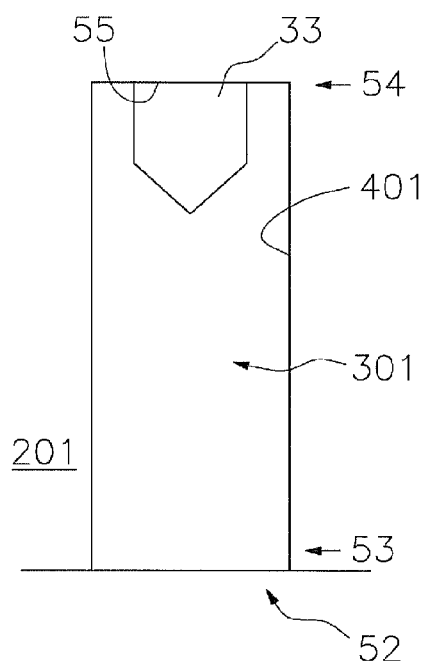
FIG. 4 is a plan view of one mode of the interior of the sensor cavity.

As shown in FIG. 4, with the sensor in this embodiment, in this mode a spacer 201 has a rectangular cutout. Left and right side walls 401 both have a planar shape, and a back wall 55 also has a planar shape.

In this case, a concave portion and/or a convex portion is provided to the bottom or the ceiling, so that a cavity 300 has a diverter.

(2) Second Mode

Figure 5:
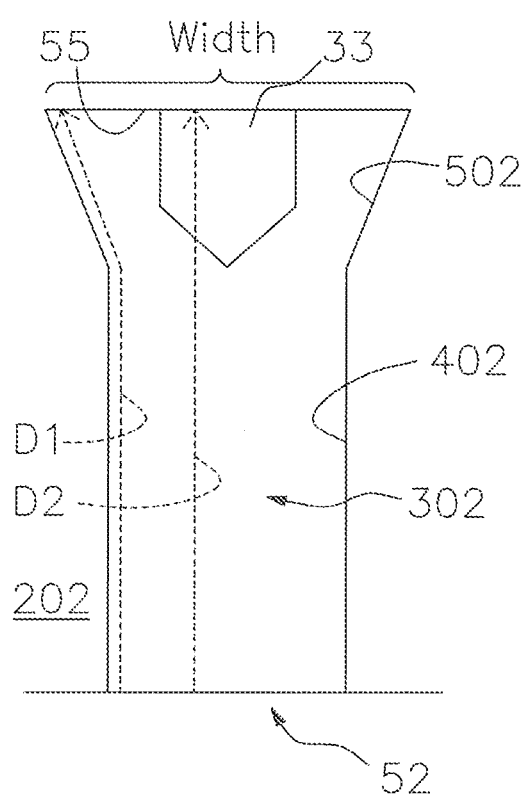
FIG. 5 is a plan view of another mode of the interior of the sensor cavity.

As shown in FIG. 5, with the sensor in this embodiment, in this mode a cutout in a spacer 202 is formed so that the sides are parallel near the suction opening 52 and spread out wider (toward the back wall 55) near the back wall 55.

That is, a triangular concave portion 502 including the back wall 55 as one of its sides is provided to left and right side walls 402 of a cavity 302. In a specific range from the suction opening 52 toward the back of the cavity 302, the left and right side walls 402 of the cavity 302 are parallel, and the distance between the left and right side walls 402 of the cavity 302 increases going toward the back.

With this configuration, the distance D1 along the side walls 402 from the suction opening 52 to the back wall 55 is greater than the linear distance D2 from the suction opening 52 to the back wall 55 (from the first end 53 to the second end 54). It is particularly favorable if the relation D1≥1.05×D2 is satisfied.

The fact that it is preferable for D1 to be greater than D2 and for the relation D1≥1.05×D2 to be satisfied also applies to FIGS. 6 to 16. It is particularly favorable for the relation D1≥1.07×D2 to be satisfied, and satisfying D1≥1.65×D2 is even better.

(3) Third Mode

Figure 6:
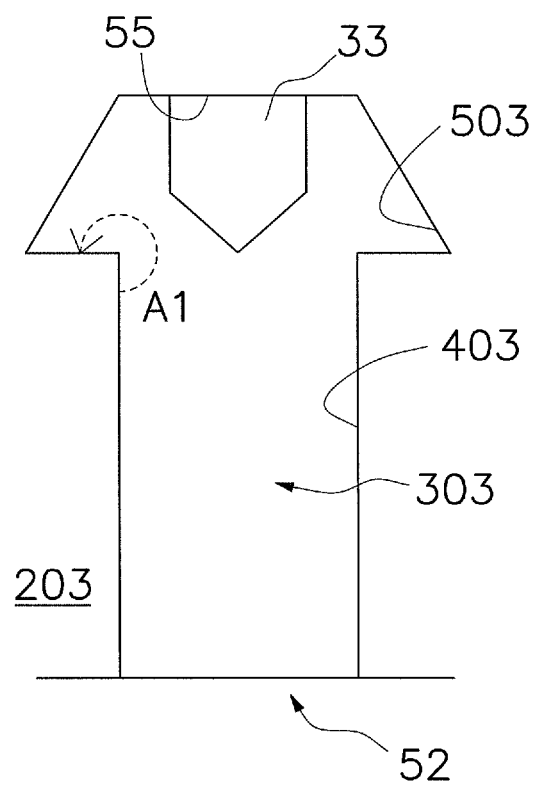
FIG. 6 is a plan view of yet another mode of the interior of the sensor cavity.

As shown in FIG. 6, in this embodiment, a spacer 203 comprises a triangular concave portion.

More specifically, a concave portion 503 is formed in left and right symmetry so that side walls 403 of a cavity 303 comprise a portion where the left and right side walls 402 of the cavity 302 are parallel from the suction opening 52 toward the back of the cavity 302, a portion where these are recessed at a right angle, and a portion where the distance between the left and right side walls 402 of the cavity 302 decreases going toward the back.

As shown in FIG. 6, the angle A1 of the concave portion with respect to the linear portion of the inner wall of the cavity is preferably at least 270 degrees.

This enhances the anti-wicking effect. The same applies regardless of the shape of the concave portion.

If the concave portion has an elliptical arc shape, then the angle of a tangent of the elliptical arc at the position on the concave portion closest to the linear portion of the inner wall of the cavity, with respect to this linear portion, is preferably at least 270 degrees.

Figure 11:
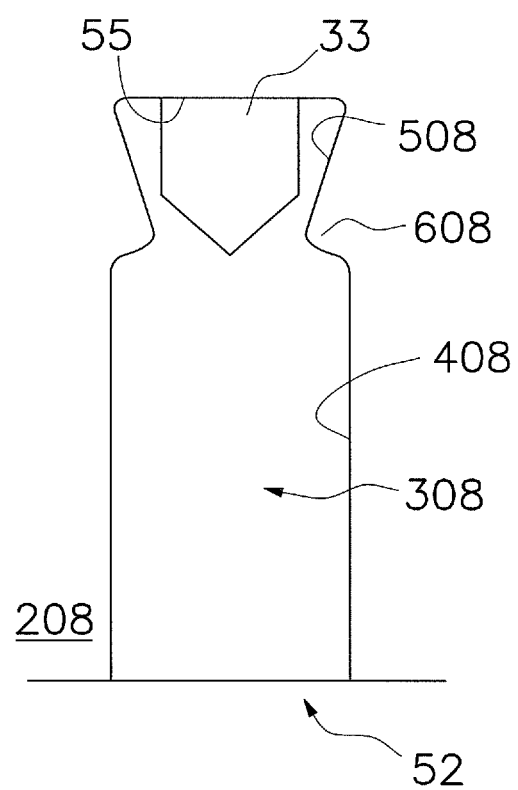
FIG. 11 is a plan view of yet another mode of the interior of the sensor cavity.

As shown in FIG. 11, however, if there is a combination of a concave portion and a convex portion, an anti-wicking effect can be easily obtained even at a smaller angle than this.

(4) Fourth Mode

Figure 7:
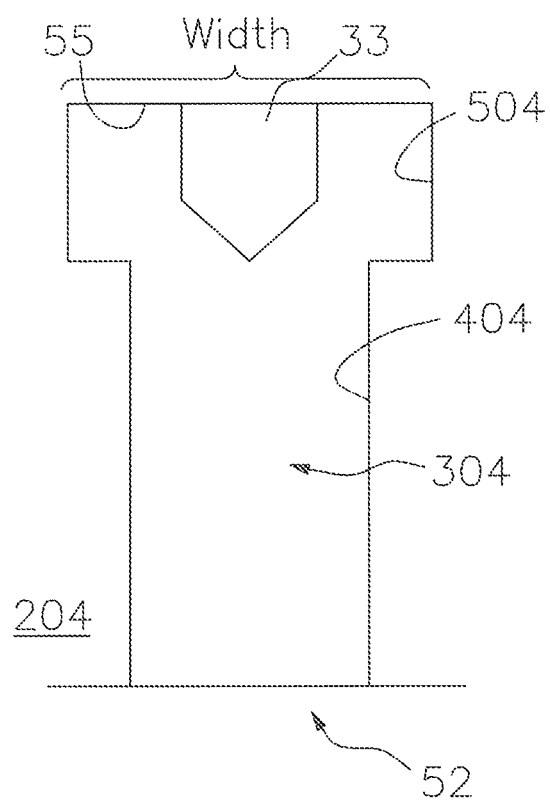
FIG. 7 is a plan view of yet another mode of the interior of the sensor cavity.

As shown in FIG. 7, with the sensor in this embodiment, a spacer 204 comprises a rectangular concave portion.

More specifically, side walls 404 of a cavity 304 comprise a concave portion 504 having an open box shape that includes the back wall 55.

(5) Fifth Mode

Figure 8:
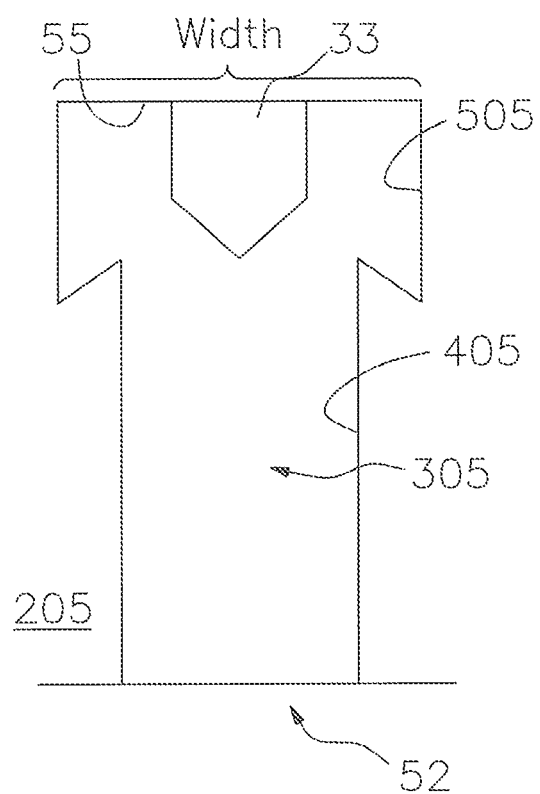
FIG. 8 is a plan view of yet another mode of the interior of the sensor cavity.

As shown in FIG. 8, with the sensor in this embodiment, a spacer 205 comprises a trapezoidal concave portion. More specifically, a concave portion 505 is formed which comprises the back wall 55 as a leg that is perpendicular to the bottom edge.

(6) Sixth Mode

Figure 9:
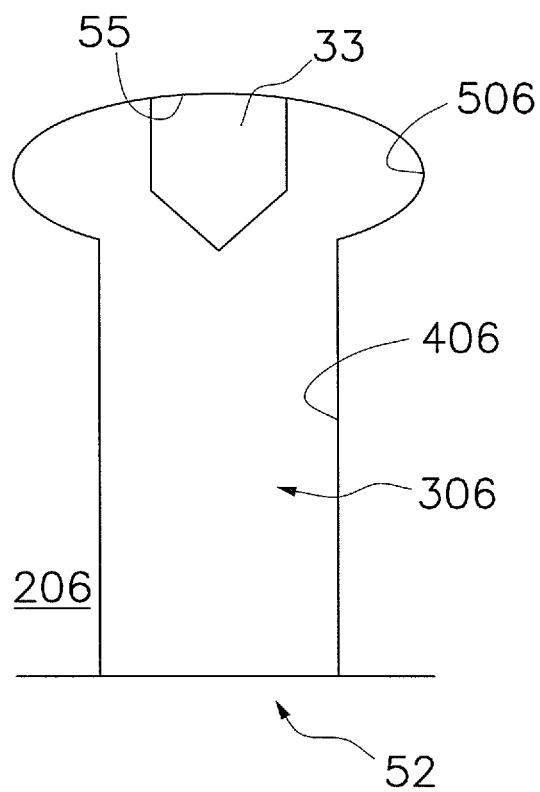
FIG. 9 is a plan view of yet another mode of the interior of the sensor cavity.

As shown in FIG. 9, with the sensor in this embodiment, a spacer 206 comprises a concave portion with an elliptical arc shape. More specifically, a concave portion 506 that comprises an elliptical arc continuous with the back wall 55 is formed in side walls 406 of a cavity 306.

(7) Seventh Mode

Figure 10:
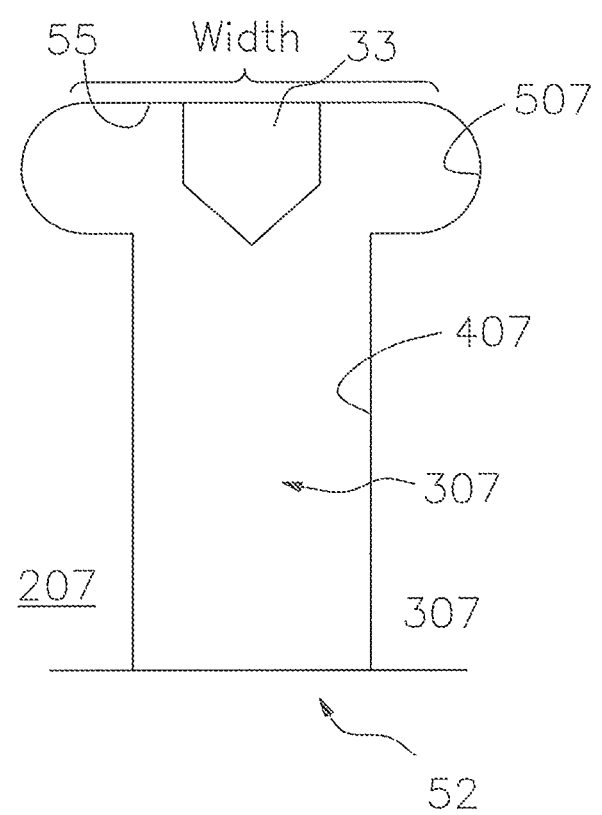
FIG. 10 is a plan view of yet another mode of the interior of the sensor cavity.

As shown in FIG. 10, with the sensor in this embodiment, a spacer 207 comprises a concave portion with a circular arc shape. More specifically, a concave portion 507 that is bounded by the planar back wall 55 and circular arc-shaped side walls 407 is formed in side walls 407 of a cavity 307.

(8) Eighth Mode

As shown in FIG. 11, with the sensor in this embodiment, a spacer 208 has a triangular convex portion. More specifically, a rounded triangular convex portion 608 is formed in side walls 408 of a cavity 308 at a position near the back wall 55. It could be said that forming the convex portion 608 forms a concave portion 508 between the convex portion 608 and the back wall 55.

Just as in this mode, all the other shapes of the cavity inner walls described in this Specification actually can have rounded corners, even though they are shown as linear corners in the drawings.

(9) Ninth Mode

With the sensor in this embodiment, the shape of the convex portion may be rectangular or fan shaped, and the position of the convex portion may be away from the back wall 55.

Figure 12:
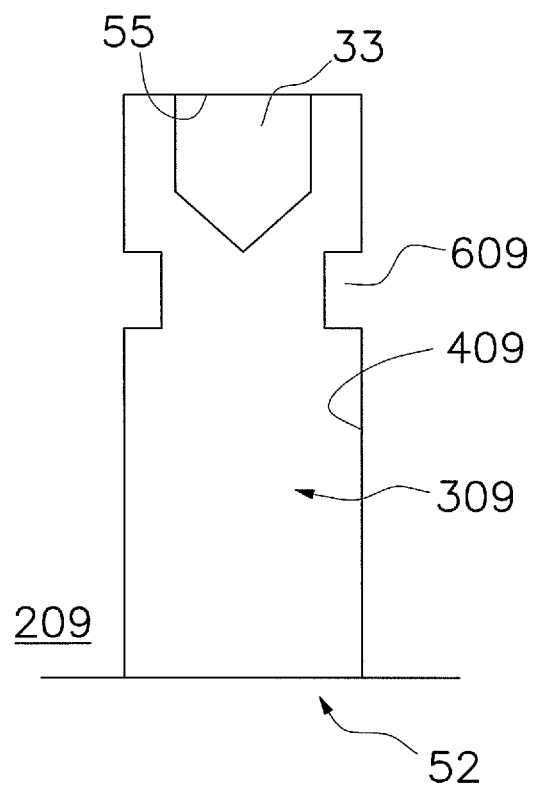
FIG. 12 is a plan view of yet another mode of the interior of the sensor cavity.

As shown in FIG. 12, a spacer 209 has a rectangular convex portion. That is, side walls 409 of a cavity 309 have a rectangular convex portion 609. The convex portion 609 is disposed between the suction opening 52 and the detecting electrode 33 at the back of the cavity 309. It could be said that providing the convex portion 609 forms a concave portion between the convex portion 609 and the back wall 55.

(10) Tenth Mode

Figure 13:
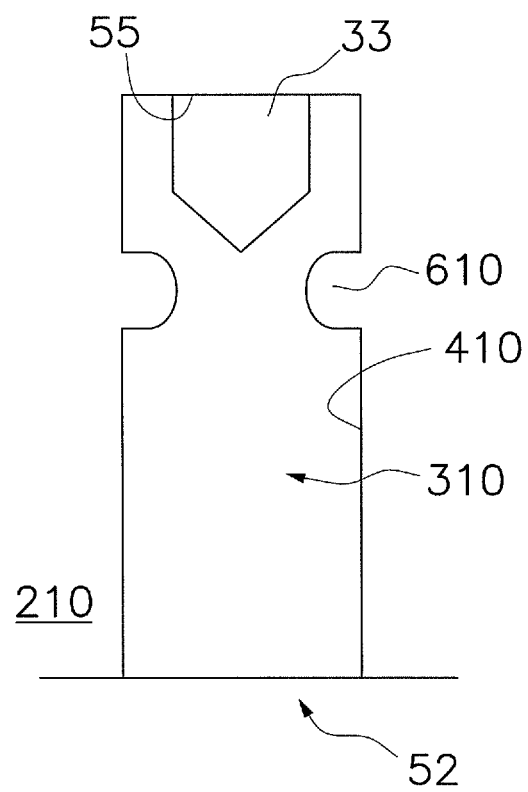
FIG. 13 is a plan view of yet another mode of the interior of the sensor cavity.

As shown in FIG. 13, with the sensor in this embodiment, a convex portion of a spacer 210 has a circular arc shape.

More specifically, side walls 410 of a cavity 310 have a convex portion 610 having a circular arc shape instead of the rectangular convex portion 609 in FIG. 12.

(11) Eleventh Mode

With the sensor in this embodiment, the fact that the inner walls of the cavity have a concave portion and a convex portion includes a case in which the inner walls of the cavity have a stepped structure.

Figure 14:
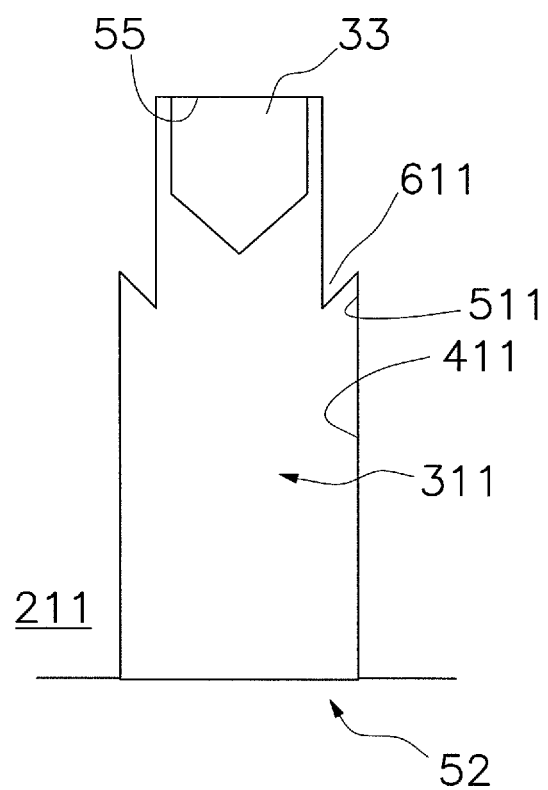
FIG. 14 is a plan view of yet another mode of the interior of the sensor cavity.

As shown in FIG. 14, a spacer 211 has a Z-shaped portion at the cutout. As a result, side walls 411 of a cavity 311 comprise a stepped structure having a concave portion 511 and a convex portion 611. The convex portion 611 protrudes toward the inside of the cavity 311 and the suction opening 52, and the concave portion 511 is recessed toward the outside of the cavity 311 and the back wall 55.

(12) Twelfth Mode

With the sensor in this embodiment, the number of concave portions and convex portions may be two or more.

Figure 15:
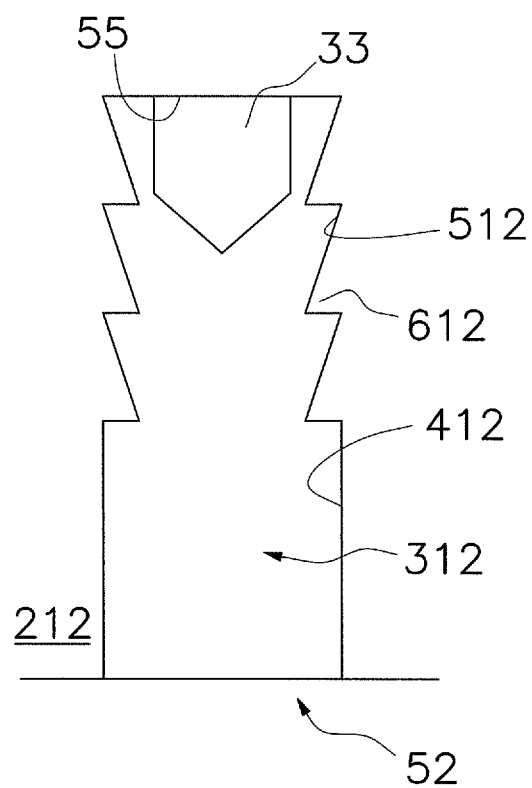
FIG. 15 is a plan view of yet another mode of the interior of the sensor cavity.

As shown in FIG. 15, if the cutout in a spacer 212 has a plurality of Z-shaped structures, a cavity 312 will comprise three convex portions 612 and concave portions 512 on each of the left and right side walls 412.

(13) Thirteenth Mode

With the sensor in this embodiment, the concave portion, just like the convex portion 610 in FIG. 13, does not need to be formed near the back wall 55.

Figure 16:
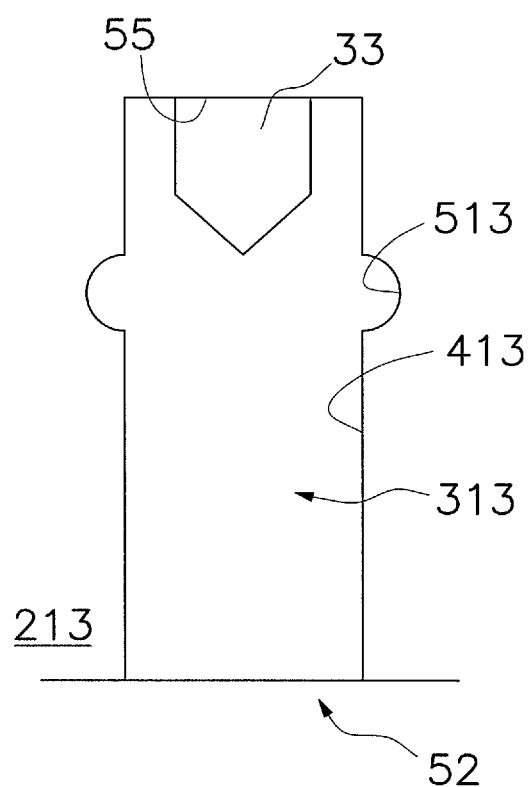
FIG. 16 is a plan view of yet another mode of the interior of the sensor cavity.

For example, as shown in FIG. 16, a spacer 213 comprises a concave portion 513 between the detecting electrode 33 and the suction opening 52, at a place corresponding to side walls 413 of a cavity 313.

(14) Fourteenth Mode

Figure 17:
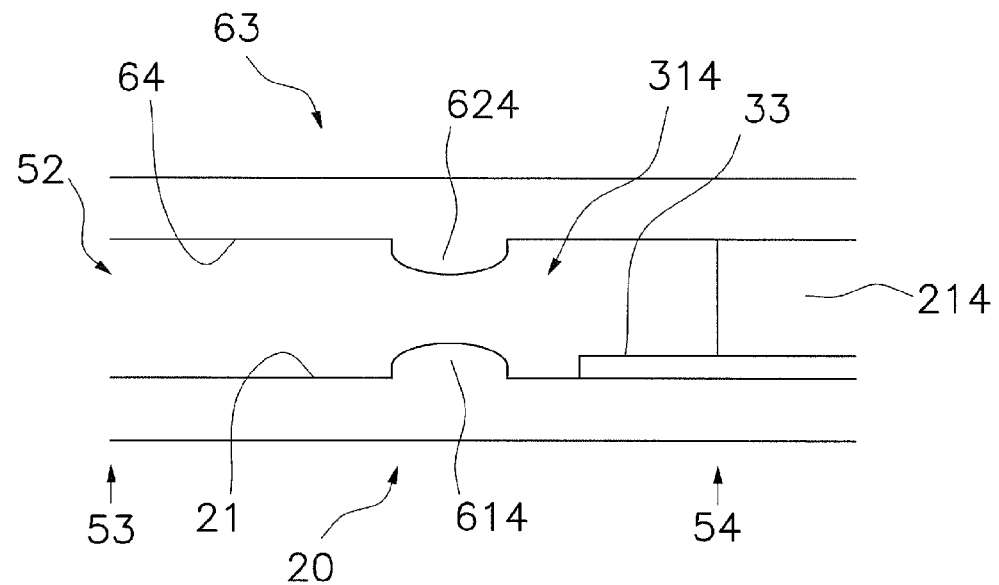
FIG. 17 is a side view of yet another mode of the interior of the sensor cavity.

As shown in FIG. 17, with the sensor in this embodiment, a substrate 20 of a sensor comprises a convex portion 614, and a cover 63 comprises a convex portion 624.

The substrate 20 and the cover 63 are disposed so that the convex portion 614 and the convex portion 624 are opposite each other. Specifically, a cavity 314 has the convex portion 624 and the convex portion 614 in vertical symmetry with a ceiling 64 and a bottom 21. The convex portion 624 and the convex portion 614 do not need to be disposed at positions of vertical symmetry, and these positions can be changed.

Instead of a convex portion, or along with a convex portion, a concave portion may be formed on the ceiling 64 and/or the bottom 21.

The spacer 214 may comprise the various convex portions or concave portions discussed above, or may comprise a flat cutout. Specifically, the ceiling and bottom on which the concave portions and/or convex portion are formed can be combined with the side walls on which the concave portions and/or convex portion are formed.

(15) Fifteenth Mode

Figure 18:
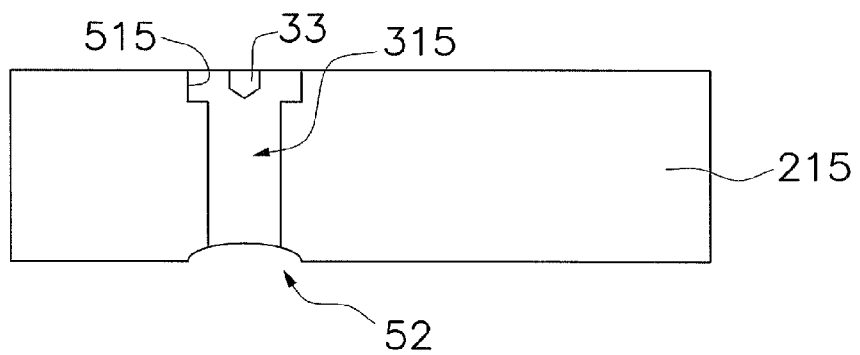
FIG. 18 is a plan view of one mode of the interior of a side-fill sensor.

As shown in FIG. 18, with the sensor in this embodiment, the diverter discussed above can also be applied to the cavity of a side-fill type of sensor.

With the side-fill sensor shown in FIG. 18, the lengthwise direction of a cavity 315 is parallel to the short-side direction of the sensor, and the suction opening 52 is provided at the end in the short-side direction of the sensor.

The detecting electrode 33 is disposed at the back of the cavity 315 as viewed from the suction opening 52. Forming a concave portion in the spacer 215 provides concave portions in left and right symmetry to the side walls at the back of the cavity 315.

(16) Sixteenth Mode

Figure 19:
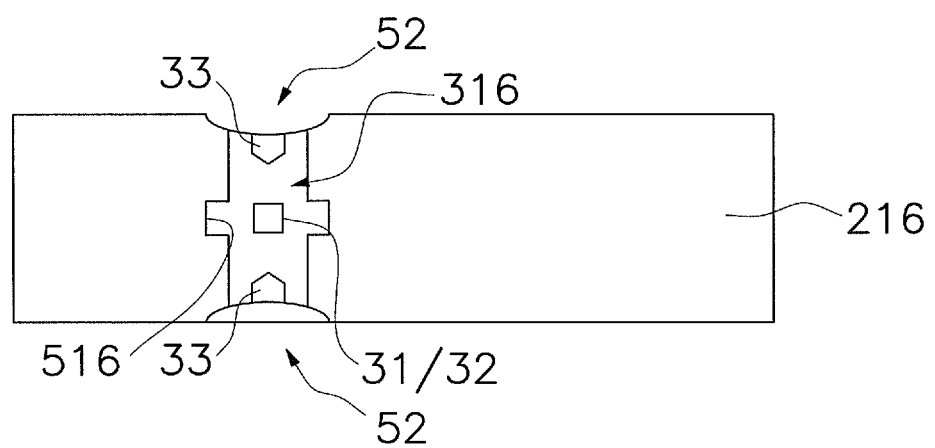
FIG. 19 is a plan view of another mode of the interior of a side-fill sensor.

As shown in FIG. 19, with the sensor in this embodiment, a side-fill sensor may comprise two suction openings 52. Specifically, a cavity 316 comprises suction openings 52 at both of its ends. A working electrode 31 and a counter electrode 32 are provided in the center of the cavity 316. The detecting electrode 33 is provided near each of the two suction openings 52. No matter in which of the suction openings 52 the sample is deposited, suction of the sample will be detected when the sample reaches the suction opening 52 on the opposite side.

In FIG. 19, a spacer 216 comprises a concave portion, so that the side walls of the cavity 316 have two rectangular concave portions 516 provided in left and right symmetry near the center in the lengthwise direction.

(17) Other

As can be seen from the above description, a configuration in which the inner walls of the cavity have a convex portion can also be called a configuration having a concave portion. The same applies to the reverse, and a configuration having a concave portion can be called a configuration having a convex portion. However, it will be understood that a concave portion will be formed if the distance between opposing inner walls is greater than the width of the cavity interior at the suction opening 52, and a convex portion will be formed if this distance is less than this width.

Wicking tends to occur in the corners of the cavity (such the corners between the side walls and ceiling, and between the side walls and the bottom), so the concave portions and convex portions are preferably provided so as to reach the corners of the cavity. However, concave portions or convex portions provided to a flat portion inside the cavity can suppress false detection such as when the biological sample seeps through to the reagent layer 4.

The concave portions and convex portions that serve as the diverter can be formed by milling the spacer with a laser, for example. The diverter can also be formed, for example, by dropping a resin onto the cover or substrate and curing, or by etching or some other method.

3. Sensor System

Figure 20:
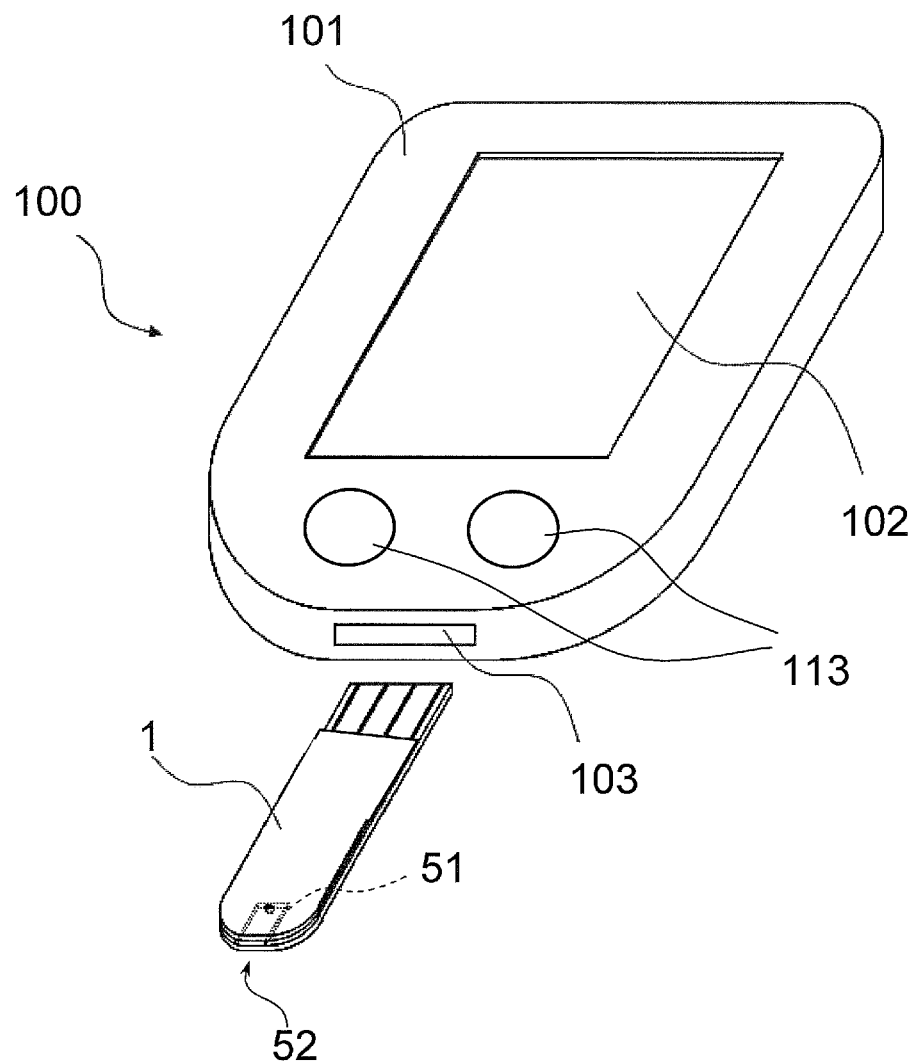
FIG. 20 is an oblique view of the simplified configuration of a sensor system.

The above-mentioned sensor 1 is used in the sensor system 100 shown in FIG. 20. The sensor system 100 has the sensor 1 and the measurement device 101.

Figure 21:
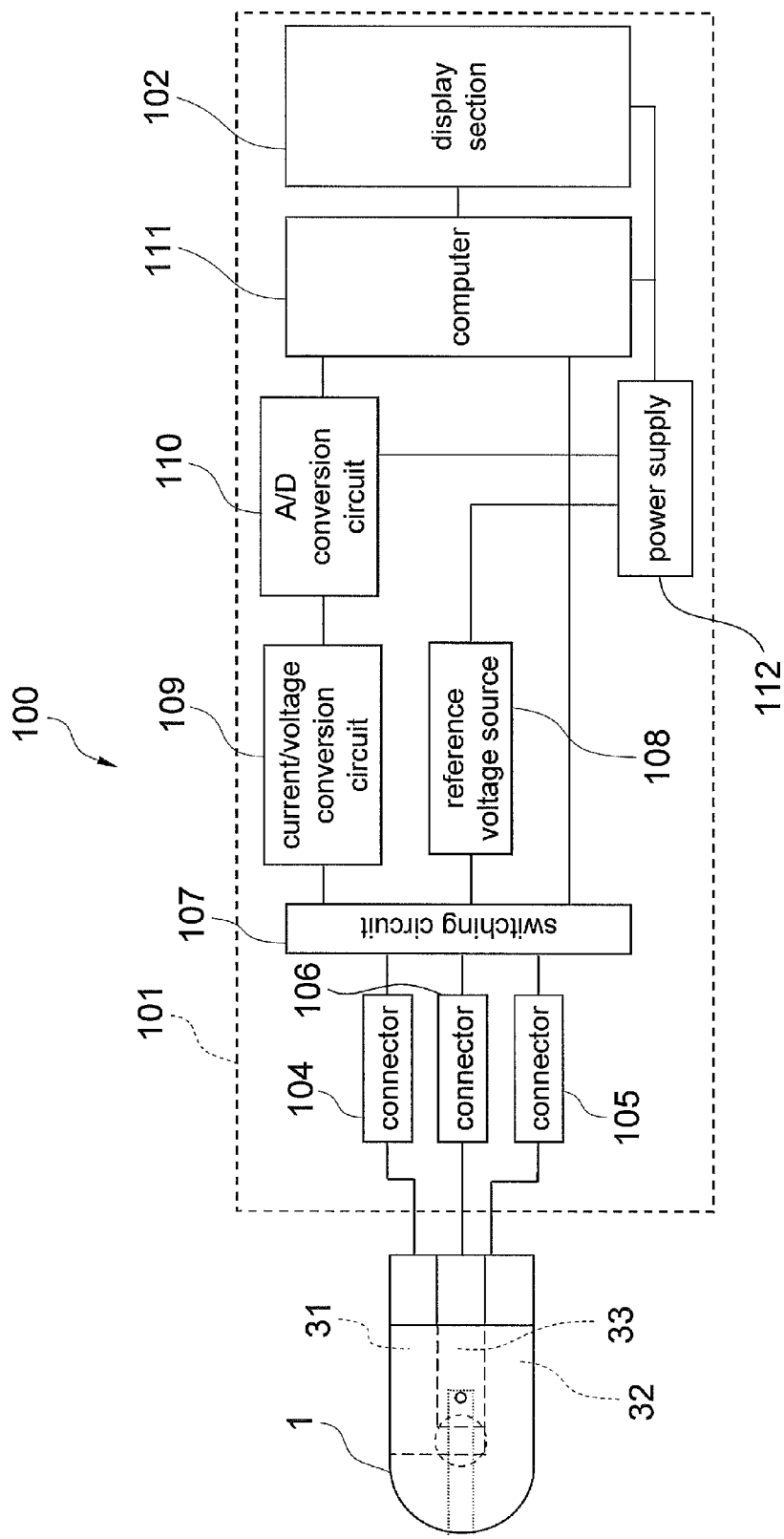
FIG. 21 is a block diagram of the simplified configuration of a sensor system.

As shown in FIGS. 20 and 21, the measurement device 101 comprises a display section 102, a mounting portion 103, a switching circuit 107, a reference voltage source 108, a current/voltage conversion circuit 109, an A/D conversion circuit 110, a computer 111, an interface section 113, and a power supply 112. The measurement device 101 further has connectors corresponding to the various electrodes of the sensor 1. In FIG. 21, the connectors 104 to 106 are shown as being provided inside the mounting portion 103.

The display section 102 displays the status of the measurement device 101, measurement results, user input details, and so forth. More specifically, the display section 102 comprises a liquid crystal display panel.

As shown in FIG. 20, the sensor 1 can be removably inserted into the mounting portion 103.

As shown in FIG. 21, the connectors 104 to 106 are connected to the electrodes 31 to 33, respectively, of the sensor 1 when the sensor 1 is mounted to the mounting portion 103.

The switching circuit 107 can connect the connectors 104 to 106 to the reference voltage source 108, and can also connect them to the current/voltage conversion circuit 109.

The reference voltage source 108 applies voltage through the connectors 104 to 106 to the electrodes 31 to 33.

The current/voltage conversion circuit 109 takes current from the sensor 1 through the connectors 104 to 106, converts it into voltage, and outputs it to the A/D conversion circuit 110.

The A/D conversion circuit 110 converts a voltage value (analog value) that is the output from the current/voltage conversion circuit 109 into a digital value.

The computer 111 has a CPU (Central Processing Unit) and a recording medium, such as a ROM (Read Only Memory) or a RAM (Random Access Memory). The computer 111 computes the concentration of a target substance, and controls the operation of the various components inside the measurement device 101.

The concentration computation function of the computer 111 will be described. The recording medium of the computer 111 stores conversion tables used in determining the concentration of a target substance in a sample, correction amount tables used in determining the amount by which this concentration is to be corrected, and so forth. The computer 111 calculates a temporary concentration of the target substance by referring to a conversion table on the basis of a pulse from the A/D conversion circuit 110. The computer 111 then uses a correction amount in the correction amount table to determine the final concentration of the target substance. The concentration thus calculated is displayed on the display section 102.

Other functions of the computer 111 besides the concentration calculation function include controlling switching of the switching circuit 107, controlling the voltage of the reference voltage source 108, measuring concentration, measuring the time during correction amount selection (timer function), outputting display data to the display section 102, and communicating with external devices.

The various functions of the computer 111 are performed when the CPU reads and executes a program stored in a ROM or the like (not shown).

The interface section 113 is provided to the surface of the measurement device 101. The interface section 113 comprises buttons or the like that are operated by the user to refer to measurement data or setting data, for example.

The power supply 112 comprises a battery or the like that supplies power to the above-mentioned various electrical circuits, display section, computer, and so on.

4. Use of Sensor System

The measurement of concentration by the sensor system 100 will now be described.

When the sensor 1 is plugged into the mounting portion 103, the connectors 104 to 106 are connected to the electrodes 31 to 33, respectively. Also, mounting the sensor 1 to the mounting portion 103 pushes down a switch (not shown) in the mounting portion 103. This switch goes ON when pushed down, and the computer 111 determines that the sensor 1 has been mounted, putting the measurement device 101 in a sample standby state. A "sample standby state" is a state in which no biological sample has yet been supplied for measurement, after the application of voltage between the working electrode 31 and the detecting electrode 33 has begun, and the measurement of current by the current/voltage conversion circuit 109 has begun.

When the user deposits a biological sample in the suction opening 52 of the sensor 1, the sample is drawn by capillary action from the suction opening 52 into the cavity 51.

Examples of samples that can be used include blood, perspiration, urine and other biological samples that come from the body. For instance, when the sensor 1 is used as a blood glucose level sensor, the user prick his own ringer, palm, arm, or the like, squeezes out a small amount of blood, and supplies this blood as a biological sample for measurement by the sensor 1.

When the biological sample reaches the working electrode 31 and the detecting electrode 33, there is a change in the current value taken by the computer 111 through the current/voltage conversion circuit 109. The computer 111 determines from this change that a biological sample has been properly drawn into the sensor 1. Measurement begins once the intake of a biological sample has thus been detected.

If no sample can be detected at the detecting electrode 33, the computer 111 performs control so that an error message prompting the deposit of more biological sample is displayed on the display section 102. As discussed above, because the cavity of the sensor 1 has a diverter, the user has enough time to add more biological sample (about 30 seconds) more a false detection occurs at the detecting electrode 33.

Inside the sensor 1, the enzymes, electron acceptors, and other such components in the reagent layer 4 dissolve into the biological sample. This causes the biological sample, the enzymes, and the electron acceptors to come into contact with each other on the electrodes 31 and 32 of the sensor 1.

The computer 111 performs control so that the switching circuit 107 connects the connector 104 and the connector 105 to the reference voltage source 108 and the current/voltage conversion circuit 109. This applies voltage between the working electrode 31 and the counter electrode 32, and the current produced between the working electrode 31 and the counter electrode 32 is transmitted to the current/voltage conversion circuit 109.

The current that flows to the current/voltage conversion circuit 109 is converted into voltage. This voltage is further converted into a digital value by the A/D conversion circuit 110. The computer 111 calculates the concentration of a particular component from this digital value. The value calculated by the computer 111 is displayed on the display section 102. Other information can also be displayed and thus conveyed to the user at this point.

Once the measurement is complete, the user can take the sensor 1 out of the mounting portion 103.

The reference voltage source 108 imparts enough voltage between the two electrodes 31 and 32 to bring about the targeted electrochemical reaction. This voltage is mainly set according to the chemical reaction and electrodes being used.

INDUSTRIAL APPLICABILITY

The present invention can be widely applied to sensors used in the detection and/or quantification of a target substance in a biological sample, such as blood glucose sensors.

GENERAL INTERPRETATION OF TERMS

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Also, the terms "part," "section," "portion," "member" or "element" when used in the singular can have the dual meaning of a single part or a plurality of parts. Also as used herein to describe the above embodiment(s), the following directional terms "forward", "rearward", "above", "downward", "vertical", "horizontal", "below" and "transverse" as well as any other similar directional terms refer to those directions of the sensor and sensor system equipped with the same. Accordingly, these terms, as utilized to describe the technology disclosed herein should be interpreted relative to sensor and sensor system equipped with the same.

The term "configured" as used herein to describe a component, section, or part of a device includes hardware and/or software that is constructed and/or programmed to carry out the desired function.

The terms of degree such as "substantially", "about" and "approximately" as used herein mean a reasonable amount of deviation of the modified term such that the end result is not significantly changed.

While only selected embodiments have been chosen to illustrate the present invention, it will be apparent to those skilled in the art from this disclosure that various changes and modifications can be made herein without departing from the scope of the invention as defined in the appended claims. For example, the size, shape, location or orientation of the various components can be changed as needed and/or desired. Components that are shown directly connected or contacting each other can have intermediate structures disposed between them. The functions of one element can be performed by two, and vice versa. The structures and functions of one embodiment can be adopted in another embodiment. It is not necessary for all advantages to be present in a particular embodiment at the same time. Every feature which is unique from the prior art, alone or in combination with other features, also should be considered a separate description of further inventions by the applicants, including the structural and/or functional concepts embodied by such feature(s). Thus, the foregoing descriptions of the embodiments according to the present invention are provided for illustration only, and not for the purpose of limiting the invention as defined by the appended claims and their equivalents.

The invention claimed is:

1. A sensor, capable of at least one of detecting and quantifying a target substance contained in a biological sample, comprising:
   a cavity including:
      a sidewall,
      a back wall,
      a first end, and
      a second end,
   the second end being on an opposite side of the cavity from the first end;
   a suction opening disposed at the first end of the cavity, the suction opening communicating the cavity to outside of the sensor;
   a working electrode disposed inside of the cavity;
   a counter electrode disposed inside of the cavity; and
   a detecting electrode disposed inside of the cavity closer to the second end than to the first end, the detecting electrode disposed toward the suction opening from the back wall and spaced apart from the side wall of the cavity;
   wherein the side wall of the cavity includes a concave portion;
   the back wall has a planar shape;
   the side wall is disposed so that the diverter is configured to extend a path from the suction opening to the detecting electrode;
   a width of the cavity along the back wall is larger than a width of the cavity along the path from the suction opening to the detecting electrode; and
   the proportions of the sensor satisfy the relationship:

$$D1 \geq 1.65 \times D2$$

in which D1 is the distance from the first end to the second end following the shortest path along a surface of the side wall of the cavity, and D2 is the linear distance from the first end to the second end.

2. A sensor system, comprising:
   the sensor according to claim 1; and
   a measurement device configured to measure the concentration of a target substance in a biological sample on the basis of a current value obtained from the sensor.

* * * * *